(12) United States Patent
Mager et al.

(10) Patent No.: US 9,801,814 B2
(45) Date of Patent: *Oct. 31, 2017

(54) TUBE FEED PACKAGES AND METHODS FOR USING SAME

(75) Inventors: Jennifer Mager, St. Paul, MN (US); Zamzam Fariba Roughead, Plymouth, MN (US); Heidi Storm, Branchburg, NJ (US); James Scott Teresi, Caldwell, NJ (US)

(73) Assignee: Nestec S.A., Vevey (CH)

( * ) Notice: Subject to any disclaimer, the term of this patent is extended or adjusted under 35 U.S.C. 154(b) by 302 days.

This patent is subject to a terminal disclaimer.

(21) Appl. No.: 13/805,784

(22) PCT Filed: Jun. 28, 2011

(86) PCT No.: PCT/US2011/042152
§ 371 (c)(1),
(2), (4) Date: Apr. 3, 2013

(87) PCT Pub. No.: WO2012/006075
PCT Pub. Date: Jan. 12, 2012

(65) Prior Publication Data
US 2013/0209373 A1    Aug. 15, 2013

Related U.S. Application Data

(60) Provisional application No. 61/359,184, filed on Jun. 28, 2010, provisional application No. 61/451,272, filed on Mar. 10, 2011.

(51) Int. Cl.
*A61K 9/00* (2006.01)
*A61K 31/20* (2006.01)
*A61K 31/70* (2006.01)
*A61K 38/02* (2006.01)
*A23L 33/00* (2016.01)
*A23L 33/17* (2016.01)
*A23L 33/115* (2016.01)
*A23L 33/16* (2016.01)
*A23L 33/125* (2016.01)
*A23L 33/15* (2016.01)
*A61K 31/202* (2006.01)
*A61K 33/00* (2006.01)
*A61J 15/00* (2006.01)

(52) U.S. Cl.
CPC .......... *A61K 9/0053* (2013.01); *A23L 33/115* (2016.08); *A23L 33/125* (2016.08); *A23L 33/15* (2016.08); *A23L 33/16* (2016.08); *A23L 33/17* (2016.08); *A23L 33/40* (2016.08); *A61K 31/20* (2013.01); *A61K 31/202* (2013.01); *A61K 31/70* (2013.01); *A61K 33/00* (2013.01); *A61K 38/02* (2013.01); *A23V 2002/00* (2013.01); *A61J 15/00* (2013.01); *B65B 2230/02* (2013.01)

(58) Field of Classification Search
CPC .................................................... A61K 9/0053
See application file for complete search history.

(56) References Cited

U.S. PATENT DOCUMENTS

| | | | |
|---|---|---|---|
| 3,990,597 A | 11/1976 | Barton | |
| 4,983,404 A * | 1/1991 | Raman | A23G 4/20 426/3 |
| 5,741,243 A | 4/1998 | Geckle | |
| 5,755,688 A * | 5/1998 | Piontek et al. | 604/83 |
| 5,760,082 A * | 6/1998 | Cook | A23C 9/1234 426/601 |
| 6,102,224 A * | 8/2000 | Sun et al. | 215/252 |
| 6,248,377 B1 * | 6/2001 | Levine | A01K 5/0114 119/711 |
| 6,346,284 B1 * | 2/2002 | Briend | A23L 25/30 424/439 |
| 8,758,832 B1 * | 6/2014 | Anderson et al. | 424/725 |
| 2002/0006455 A1 * | 1/2002 | Levine | 426/104 |
| 2004/0197381 A1 * | 10/2004 | Kanie | A61K 47/36 424/439 |
| 2006/0210592 A1 | 9/2006 | Kodsi | |
| 2010/0152107 A1 | 6/2010 | Le-Henand et al. | |

FOREIGN PATENT DOCUMENTS

| | | |
|---|---|---|
| CN | 1257731 | 6/2000 |
| EP | 0350469 | 1/1990 |
| JP | 63198954 | 8/1988 |
| JP | 2004300103 | 10/2004 |
| JP | 2005154401 | 6/2005 |
| JP | 2007502280 | 2/2007 |
| JP | 2009072094 | 4/2009 |
| JP | 2010075553 | 4/2010 |
| JP | 2011207791 | 10/2011 |
| WO | 9958001 | 11/1999 |
| WO | 2007104023 | 9/2007 |

OTHER PUBLICATIONS

Q. Huang, et al., "Influence of Comprehensive Nursing Interventions on Anxiety and Depression of Elderly Nasal Feeding Patients," Journal of Nursing (China), vol. 15, No. 9, Sep. 2008, 5 pages.

(Continued)

*Primary Examiner* — Benjamin Packard
(74) *Attorney, Agent, or Firm* — K&L Gates LLP

(57) ABSTRACT

Nutritional compositions that mimic whole foods and methods of using the nutritional compositions are provided. The nutritional compositions may include an increased number and variety of fruits and vegetables, an increased variety of macronutrient sources and an increased amount of other components that are found in whole foods. The nutritional compositions may also include ethnicity-specific meals and organic ingredients and provide emotional appeal to the patient and/or the patient's caregiver. Methods of administering such nutritional compositions to patients in need of same are also provided.

12 Claims, No Drawings

(56) References Cited

OTHER PUBLICATIONS

Nemoto et al. "Development of a Method of Providing Tube-Fed Patients With Eating Sensation and Satiation" Kaken: Database of Grants-in-Aid for Scientific Research, Japan, 2004, Research Project No. 15659520, https://kaken.nii.ac.jp/d/p/15659520/2003/3/ja.ja.html, 1 page.

Japanese Office Action for Application No. P2013-518568, Dispatch No. 074625, dated Feb. 24, 2015, 9 pages.

Munakata et al. "Olfactory Stimulation Using Black Pepper Oil Facilitates Oral Feeding in Pediatric Patients Receiving Long-Term Enteral Nutrition" Tohoku Journal of Experimental medicine, vol. 214, 2008, pp. 327-332.

Dintinjana et al. "Nutritional and Pharmacologic Support in Patients with Pancreatic Cancer" Collegium Antropologicum, vol. 32(2), 2008, pp. 505-508.

Tchekmedyian et al. "Clinical Aspects of Nutrition in Advanced Cancer" Oncology, vol. 49 (Suppl. 2), 1992, pp. 3-7.

Australia Office Action for Patent No. 2011276546, dated Mar. 26, 2015, 4 pages.

Japanese Office Action for Application No. P2013-518568, Dispatch No. 474633, dated Oct. 20, 2015, 7 pages.

\* cited by examiner

TUBE FEED PACKAGES AND METHODS FOR USING SAME

CROSS REFERENCE TO RELATED APPLICATIONS

The present application is a National Stage of International Application No. PCT/US2011/042152, filed on Jun. 28, 2011, which claims priority to U.S. Provisional Patent Application No. 61/359,184, filed Jun. 28, 2010, and U.S. Provisional Patent Application No. 61/451,272, filed Mar. 10, 2011, the entire contents of which are being incorporated herein by reference.

SUMMARY

Nutritional compositions including whole foods are provided. Methods of using the nutritional compositions are also provided. In a general embodiment, the present disclosure provides a nutritional composition (e.g., oral nutritional supplements, tube feed formulations, etc.) including at least five different processed whole food components; a source of protein, a source of fat, a source of carbohydrate, and a source of vitamins and minerals.

In an embodiment, the five different processed whole food components may include 4 servings of fruits/vegetables and 1 serving of an animal source.

In an embodiment, the nutritional composition includes at least six or seven different whole food components.

In an embodiment, the whole food components are selected from the group consisting of a processed fruit, a processed vegetable, a processed meat, a processed grain, or combinations thereof. In an embodiment, the whole food components need not be processed.

In an embodiment, the nutritional composition further includes at least one of an herb, a spice and a flavoring.

In an embodiment, the protein is selected from the group consisting of dairy based proteins, plant based proteins, animal based proteins, artificial proteins, or combinations thereof.

In an embodiment, the dairy based proteins are selected from the group consisting of casein, caseinates, casein hydrolysates, whey, whey hydrolysates, milk protein concentrate, milk protein isolate, or combinations thereof.

In an embodiment, the plant based proteins are selected from the group consisting of soy protein, pea protein, canola protein, wheat and fractionated wheat proteins, corn proteins, zein proteins, rice proteins, oat proteins, potato proteins, peanut proteins, proteins derived from beans, lentils, buckwheat, pulses, or combinations thereof.

In an embodiment, the animal based proteins are selected from the group consisting of beef, poultry, fish, lamb, seafood, pork, egg, or combinations thereof.

In an embodiment, the nutritional composition further includes phospholipids.

In an embodiment, the nutritional composition further includes a prebiotic selected from the group consisting of acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

In an embodiment, the nutritional composition further includes a probiotic selected from the group consisting of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

In an embodiment, the nutritional composition further includes an amino acid selected from the group consisting of alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

In an embodiment, the nutritional composition further includes a source of $\omega$-3 fatty acids selected from the group consisting of $\alpha$-linolenic acid, docosahexaenoic acid, eicosapentaenoic acid, or combinations thereof. The source of $\omega$-3 fatty acids may be selected from the group consisting of fish oil, poultry, eggs, flax seed, walnuts, almonds, algae, krill, modified plants, or combinations thereof.

In an embodiment, the nutritional composition further includes a nucleotide. The nucleotide may be selected from the group consisting of a subunit of deoxyribonucleic acid, a subunit of ribonucleic acid, a polymeric form of deoxyribonucleic acid, a polymeric form of ribonucleic acid, yeast extract forms, or combinations thereof.

In an embodiment, the nutritional composition further includes a phytonutrient that is isolated from food or is present as part of the whole food component provided in the tube feed formula (fruits, vegetables, grains). These may be flavanoids, carotenoids, allied phenolic compounds, polyphenolic compounds, terpenoids, alkaloids, sulphur-containing compounds, or combinations thereof.

In an embodiment, the nutritional composition further includes ingredients with antioxidant activities selected from the group consisting of herbs/spices/flavorings (garlic, cinnamon, ginseng, turmeric, curcumin, rosemary, mint, lemongrass, ginkgo, ginger, tea, vanilla extract), polyphenols, carotenoids, flavonoids, lignan, lutein, lycopene coenzyme Q10 ("CoQ10"), glutathione Goji (wolfberry), lacto-wolfberry, hesperidine, selenium, vitamin A, vitamin E, or combinations thereof.

In an embodiment, the vitamins are selected from the group consisting of vitamin A, vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid), and vitamin B 12 (various cobalamins; commonly cyanocobalamin in vitamin supplements), vitamin C, vitamin D, vitamin E, vitamin K, folic acid, biotin, choline, or combinations thereof.

In an embodiment, the minerals are selected from the group consisting of boron, calcium, chromium, copper, iodine, iron, magnesium, manganese, molybdenum, nickel, phosphorus, potassium, selenium, silicon, tin, vanadium, zinc, or combinations thereof.

In an embodiment, the nutritional composition further includes a nutrient source that is typically consumed by individuals in a specific region of the world. For example, the nutrient source may be a fruit, a vegetable, protein, an herb, a spice, a flavoring, or combinations thereof.

In an embodiment, the nutritional composition includes pediatric-friendly food blends, or foods that parents would consider "normal" for kids consuming an oral diet. Popular branded foods include, for example, Cheerios®, Juicy Juice®, Campbell's Alphabet Soup™, chicken nuggets, strawberry shortcake, bananas, apple sauce, etc.

In an embodiment, the whole food components (e.g., fruit, vegetable, grain), vitamins, minerals, proteins, fats, and/or carbohydrates are organic. In one embodiment, the protein source may be raised with natural farming practices including free range (chicken), lamb and grass grazing (beef).

In an embodiment, the nutritional composition includes a source of fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

In another embodiment, the nutritional composition includes a processed whole food, at least seven different sources of macronutrients selected from the group consisting of protein, carbohydrate, fat, or combinations thereof, and a source of vitamins or minerals. The sources of macronutrients may be selected from fats, carbohydrates and proteins.

In an embodiment, the at least seven different sources of macronutrients include at least one protein, at least one carbohydrate and at least one fat.

In an embodiment, the at least seven different sources of macronutrients include at least three different protein sources.

In an embodiment, the at least seven different sources of macronutrients include at least three different carbohydrate sources.

In an embodiment, the at least seven different sources of macronutrients include at least three different fat sources.

In yet another embodiment, a method of improving the overall health of a patient having an underlying medical condition is provided. The method includes administering to a patient having an underlying medical condition a nutritional composition having at least five different whole food components; a source of protein, a source of fat, carbohydrate, and a source of vitamins and minerals.

In an embodiment, the nutritional composition includes at least six or seven different whole food components.

In an embodiment, the whole food components are selected from the group consisting of a processed fruit, a processed vegetable, a processed meat, a processed grain, a herb, spice or flavoring, or combinations thereof.

In an embodiment, the patient uses the nutritional composition for a long-term to receive nutrients found in whole food. The patient may be sedentary/bedridden and/or may be an older adult. The patient may have depressed or altered immune function and increased oxidative stress, compromised gut health, altered glucose metabolism and lipid status, poor musculoskeletal health (loss of bone and muscle), pressure ulcers, and chronic wounds. In an embodiment, the patient may also have an underlying medical condition selected from the group consisting of cerebral palsy, failure-to-thrive, cystic fibrosis, neuromuscular disorders, brain injury, developmental delay, or combinations thereof.

In another embodiment, a method of maintaining or improving the overall health of a patient using a tube feeding or nutritional composition for a long-term or having an underlying medical condition is provided. The method includes administering to a patient having an underlying medical condition a nutritional composition having a processed whole food, a source of vitamins or minerals, and at least seven different sources of macronutrients selected from the group consisting of protein, carbohydrates, fats, or combinations thereof.

In an embodiment, the nutritional composition contains at least seven different sources of macronutrients with the sources including at least one source of protein, at least one source of carbohydrate, and at least one source of fat. The nutritional composition may also include a source of fiber. The nutritional composition may contain at least seven different sources of macronutrients that may also include at least three different proteins. The nutritional composition may contain at least seven different sources of macronutrients that may also include at least three different carbohydrates. The nutritional composition may contain at least seven different sources of macronutrients that may also include at least three different fats. The nutritional composition may also include at least three different sources of fiber.

In another embodiment, methods of administering nutritional composition are provided. The methods include administering a nutritional composition as a bolus, at three or more different times per day. The first nutritional composition having a whole food to a patient at a first time of a day may correspond to a typical breakfast time, administering a second nutritional composition having a whole food to the patient at a second time of the day may correspond to a typical lunch time, and administering a third nutritional composition having a whole food to the patient at a third time of the day may correspond to a typical dinner time. Additional bolus tube feeding may correspond to snack times. As such, the present methods may include fourth, fifth or sixth nutritional compositions corresponding to typical daily snack times.

In an embodiment, the nutritional compositions are changed to a new nutritional composition on a daily basis. The nutritional compositions may also be changed to a new nutritional composition on a weekly or monthly basis. The cycle of different nutritional compositions may occur by different weeks. In these respects, for example, the methods may provide a new first, or breakfast, formulation each day of the week. The methods may also provide a new second, or lunch, formulations each day of the week. In another embodiment, the nutritional composition may be the same for each of breakfast, lunch and dinner for a first week, and then changed to a second formulation for each of breakfast, lunch and dinner for a second week, etc.

In an embodiment, the first, second and third nutritional compositions include at least one source of protein, at least one source of carbohydrate, at least one source of fat, and at least one type of fruit and vegetable. The protein of each of the first, second and third nutritional compositions may be different. At least one of a fruit and a vegetable of each of the first, second and third nutritional compositions may be different.

In an embodiment, the nutritional composition may contain food components specific to cultures/regions of the world (e.g., Mediterranean, Asia, South and Latin America).

In an embodiment, the amount/bolus of nutrients provided at a single time point (resulting in a more concentrated dose) may elicit different physiological responses compared to when provided as a continuous feed. As an example, pulse feeding of protein stimulates protein synthesis to a greater extent than when protein is consumed evenly throughout the day. In an embodiment, at least one tube feeding formulation per day may contain high amounts of protein.

In an embodiment, increased variety of foods and/or food components and flavors may be delivered to stimulate specific taste receptors in the gut, thus eliciting different physiological responses. For example, stimulation of the Umami taste receptor in the gut increases mucous secretion and GLP-1 and GLP-2 release. Stimulation of the bitter taste receptor in the gut increases CCK release and delays gastric emptying. Stimulation of the sweet taste receptor in the gut stimulates release of GLP-1 and GIP, and also regulates the expression of glucose transporter thus enhancing gut absorption of sugars.

In an embodiment, the nutritional compositions may be delivered warm or cold. It can be theorized that differences in food temperature may impact digestion and physiological response.

In yet another embodiment, a tube feed package is provided. The package includes a first component contained in the package that is a tube feed formulation having a processed whole food, and a second component contained in the package, the second component being ingestible and packaged separately from the first component. The second component may include a taste, or an aroma that may stimulate the cephalic phase of digestion, and/or include functional ingredients such as probiotics for oral health.

In an embodiment, the second component is a tablet, lozenge, dissolvable strip, or chewing gum that contains a flavor and scent, and may or may not contain a source of protein, a source of fat or a source of carbohydrate. The tablet, lozenge, dissolvable strip or chewing gum would simulate the experience of eating and stimulate the cephalic response, which primes the body to absorb and use nutrients. The second component may be compliant with a nothing per orem ("NPO") diet. The second component may also be calorie free and may also have a scratch and sniff component. The second component may release a scent upon opening.

In an embodiment, the flavor of the second component corresponds to the processed whole food of the tube feed formulation. The flavor and/or scent of the second component may also correspond to a nutrient source that is typically consumed by individuals in a specific region of the world.

In an embodiment, the second component includes a functional ingredient selected from the group consisting of probiotics, capsaisin, a source of strong flavor, or combinations thereof. The second component may have a strong flavor (e.g., tart, ginger, etc. to stimulate saliva production), and contain functional ingredients such as probiotics (to maintain healthy oral flora), and/or ingredients that trigger the swallow reflex such as capsaicin. The second component may be, or have a, scratch and sniff component to enhance the aroma, and may be used when oral intake is contraindicated (e.g., dysphagia, neurological impairment).

In an embodiment, the flavor and scent of the second component may or may not be similar to the foods present in the tube feeding. In another embodiment, the second component comes with a variety of flavors for emotional appeal such that the patient can choose what they are hungry for.

In an embodiment, the first and second components are contained in a package having a shape of an eating utensil (e.g., a plate) with pictures or shapes of food components found in the tube feed formula, or combinations thereof.

An advantage of the present disclosure is to provide improved tube feed formulations.

Another advantage of the present disclosure is to provide improved nutritional compositions that include real or whole foods.

Yet another advantage of the present disclosure is to provide nutritional compositions that promote bone health.

Still yet another advantage of the present disclosure is to provide nutritional compositions that preserve lean body mass.

Still yet another advantage of the present disclosure is to provide nutritional compositions that preserve muscle mass.

Another advantage of the present disclosure is to provide nutritional compositions that maintain glucose homeostasis.

Another advantage of the present disclosure is to provide nutritional compositions that maintain normal or reduce cholesterol or triglycerides levels.

Another advantage of the present disclosure is to provide nutritional compositions that maintain gut health.

Another advantage of the present disclosure is to provide nutritional compositions that help maintain healthy immune function and reduce oxidative stress.

Another advantage of the present disclosure is to provide nutritional compositions that support normal growth.

Another advantage of the present disclosure is to provide nutritional compositions that treat and/or prevent chronic diseases.

Yet another advantage of the present disclosure is to provide nutritional compositions that treat and/or prevent pressure ulcers.

An advantage of the present disclosure is to provide nutritional compositions that improve the overall health of patients on a long-term tube feeding regimen. These patients may be sedentary, elderly, or have cystic fibrosis, quadriplegia, cerebral palsy, and/or other neuromuscular disorders, or dysphagia.

Still yet another advantage of the present disclosure is to provide tube feed formulations that provide emotional appeal to patients and/or their caregivers.

Another advantage of the present disclosure is to provide tube feed formulations that mimic a real food, oral diet.

Yet another advantage of the present disclosure is to provide methods of administering tube feed formulations that simulate administration of normal meals.

Additional features and advantages are described herein, and will be apparent from the following Detailed Description.

DETAILED DESCRIPTION

As used herein, "about" is understood to refer to numbers in a range of numerals. Moreover, all numerical ranges herein should be understood to include all integer, whole or fractions, within the range.

As used herein the term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione Goji (wolfberry), hesperidine, lactowolfberry, lignan, lutein, lycopene, polyphenols, selenium, vitamin A, vitamin C, vitamin E, zeaxanthin, or combinations thereof.

As used herein, "complete nutrition" includes nutritional products and compositions that contain sufficient types and levels of macronutrients (protein, fats and carbohydrates) and micronutrients to be sufficient to be a sole source of nutrition for the animal to which it is being administered to. Patients can receive 100% of their nutritional requirements from such complete nutritional compositions.

As used herein, "effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

While the terms "individual" and "patient" are often used herein to refer to a human, the invention is not so limited. Accordingly, the terms "individual" and "patient" refer to any animal, mammal or human having or at risk for a medical condition that can benefit from the treatment.

As used herein, non-limiting examples of sources of ω-3 fatty acids such α-linolenic acid ("ALA"), docosahexaenoic acid ("DHA") and eicosapentaenoic acid ("EPA") include fish oil, poultry, eggs, or other plant or nut sources such as flax seed, walnuts, almonds, algae, krill, modified plants, etc.

As used herein, "food grade micro-organisms" means micro-organisms that are used and generally regarded as safe for use in food.

As used herein, "incomplete nutrition" includes nutritional products or compositions that do not contain sufficient levels of macronutrients (protein, fats and carbohydrates) or micronutrients to be sufficient to be a sole source of nutrition for the animal to which it is being administered to. Partial or incomplete nutritional compositions can be used as a nutritional supplement.

As used herein, "long term administrations" are preferably continuous administrations for more than 6 weeks. Alternatively, "short term administrations," as used herein, are continuous administrations for less than 6 weeks.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

As used herein, "normal bone growth" refers to the process by which childhood and adolescent bones are sculpted by modeling, which allows for the formation of new bone at one site and the removal of old bone from another site within the same bone. This process allows individual bones to grow in size and to shift in space. During childhood bones grow because resorption (the process of breaking down bone) occurs inside the bone while formation of new bone occurs on its outer (periosteal) surface. At puberty the bones get thicker because formation can occur on both the outer and inner (endosteal) surfaces. The remodeling process occurs throughout life and becomes the dominant process by the time that bone reaches its peak mass (typically by the early 20 s). In remodeling, a small amount of bone on the surface of trabeculae or in the interior of the cortex is removed and then replaced at the same site. The remodeling process does not change the shape of the bone, but it is nevertheless vital for bone health. Modeling and remodeling continue throughout life so that most of the adult skeleton is replaced about every 10 years. While remodeling predominates by early adulthood, modeling can still occur particularly in response to weakening of the bone.

As used herein, a "nucleotide" is understood to be a subunit of deoxyribonucleic acid ("DNA") or ribonucleic acid ("RNA"). It is an organic compound made up of a nitrogenous base, a phosphate molecule, and a sugar molecule (deoxyribose in DNA and ribose in RNA). Individual nucleotide monomers (single units) are linked together to form polymers, or long chains. Exogenous nucleotides are specifically provided by dietary supplementation. The exogenous nucleotide can be in a monomeric form such as, for example, 5'-Adenosine Monophosphate ("5'-AMP"), 5'-Guanosine Monophosphate ("5'-GMP"), 5'-Cytosine Monophosphate ("5'-CMP"), 5'-Uracil Monophosphate ("5'-UMP"), 5'-Inosine Monophosphate ("5'-IMP"), 5'-Thymine Monophosphate ("5'-TMP"), or combinations thereof. The exogenous nucleotide can also be in a polymeric form such as, for example, an intact RNA. There can be multiple sources of the polymeric form such as, for example, yeast RNA.

"Nutritional products," or "nutritional compositions," as used herein, are understood to include any number of optional additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein the term "patient" is understood to include an animal, especially a mammal, and more especially a human that is receiving or intended to receive treatment, as it is herein defined.

As used herein, "phytochemicals" or "phytonutrients" are non-nutritive compounds that are found in many foods. Phytochemicals are functional foods that have health benefits beyond basic nutrition, and are health promoting compounds that come from plant sources. Non-limiting examples of phytonutrients, or phytochemicals, include those that are flavonoids and allied phenolic and polyphenolic compounds, terpenoids such as carotenoids, alkaloids and sulphur-containing compounds; including curcumin, limonin, and quercetin or combinations thereof.

As used in this disclosure and the appended claims, the singular forms "a," "an" and "the" include plural referents unless the context clearly dictates otherwise. Thus, for example, reference to "a polypeptide" includes a mixture of two or more polypeptides, and the like.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the GI tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125: 1401-1412 (1995). Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A. Benno Y. et al., *Probiotics: how should they be defined?*, Trends Food Sci. Technol. 1999:10, 107-10 (1999). In general, it is believed that these micro-organisms inhibit or influence the growth and/or metabolism of pathogenic bacteria in the intestinal tract, and may also influence the microflora in the mouth. The probiotics may also activate the immune function of the host. For this reason, there have been many different approaches to include probiotics into food products. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

As used herein, a "processed whole food" is a whole food that has been modified from its natural or prepared state and is in a state so that it can be placed into a tube feed formulation.

The terms "protein," "peptide," "oligopeptides" or "polypeptide," as used herein, are understood to refer to any composition that includes, a single amino acid (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of sources of proteins include dairy based proteins, plant based proteins, animal based proteins and artificial proteins. Dairy based proteins include, for example, casein, casein hydrolysates, caseinates (e.g., all forms including sodium, calcium, potassium caseinates), whey hydrolysates, whey (e.g., all forms including concentrate, isolate, demineralized), milk protein concentrate, and milk protein isolate. Plant based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, and any proteins derived from beans, buckwheat, lentils, and pulses. Animal based proteins may include, for example, beef, poultry, fish, lamb, seafood, pork, egg, or combinations thereof.

All dosage ranges contained within this application are intended to include all numbers, whole or fractions, contained within said range.

As used herein, a "synbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein, a "tube feed" is a complete or incomplete nutritional product or composition that is administered to an animal's gastrointestinal system, other than through oral administration, including but not limited to a nasogastric tube, orogastric tube, gastric tube, jejunostomy tube ("J-tube"), percutaneous endoscopic gastrostomy ("PEG"), port, such as a chest wall port that provides access to the stomach, jejunum and other suitable access ports.

As used herein the term "vitamin" is understood to include any of various fat-soluble or water-soluble organic substances non-limiting examples include choline, vitamin A, vitamin B1 (thiamine), vitamin B2 (riboflavin), vitamin B3 (niacin or niacinamide), vitamin B5 (pantothenic acid), vitamin B6 (pyridoxine, pyridoxal, or pyridoxamine, or pyridoxine hydrochloride), vitamin B7 (biotin), vitamin B9 (folic acid), and vitamin B12 (various cobalamins; commonly cyanocobalamin in vitamin supplements), vitamin C, vitamin D, vitamin E, vitamin K, folic acid and biotin) essential in minute amounts for normal growth and activity of the body and obtained naturally from plant and animal foods or synthetically made, pro-vitamins, derivatives, analogs.

In an embodiment, a source of vitamins or minerals can include at least two sources or forms of a particular nutrient. This represents a mixture of vitamin and mineral sources as found in a mixed diet, and may include natural forms. Also, a mixture may also be protective in case an individual has difficulty absorbing a specific form, a mixture may increase uptake through use of different transporters, or may offer a specific health benefit. As an example, there are several forms of vitamin E, with the most commonly consumed and researched being tocopherols (alpha, beta, gamma, delta) and less commonly tocotrienols (alpha, beta, gamma, delta), which all vary in biological activity. There is a structural difference such that the tocotrienols can more freely move around the cell membrane; several studies report various health benefits related to cholesterol levels, immune health, and reduced risk of cancer development. A mixture of tocopherols and tocotrienols would cover the range of biological activity.

The source of selenium can be of inorganic (e.g., selenite, selenate) or organic in origin (e.g., selenomethionine, selenocysteine, seelnoyeast), all occurring in a habitual mixed diet. Inorganic and organic have distinct, complementary uptake and distribution mechanisms in the body, thus allowing to optimize selenium provision to the body.

As used herein, "whole food," "whole food component," "real food" or "real food component" is understood to mean a food typically ingested by an individual in a normal daily diet when the food is in its natural or prepared state as opposed to any reduced components of the food. For example, a whole food may include any known fruits, vegetables, grain, meats or sources of protein, carbohydrate or fat. The "whole food," "whole food component," "real food" or "real food component" may be processed so they can be used in a tube feed. In an embodiment, this processing is minimal to keep it as close to the "unprocessed" food as possible, and still be usable in the tube feed. The skilled artisan will appreciate that the use of a "whole food," "whole food component," "real food" or "real food component" does not limit the use of other nutrient sources. For example, powdered fruits and vegetables may also be included in the compositions.

As used herein, "zoo-chemicals" refers to functional foods that have health benefits beyond basic nutrition, and are health promoting compounds that are found in animal sources.

Patients that are either inactive or fed one single formula diet for a significant amount of time are susceptible to metabolic disturbances that may result from a lack of variety or proper nutrient values in their diets. For example, long-term tube-fed patients may suffer from such disturbances. Although the basic nutritional needs of the patient may be met through tube feeding, current formulas for tube feeding are not optimized for maintenance of patient health over long time periods.

Patients who receive long-term tube feeds often remain on a single dietary source for weeks, months, or even years. Therefore, the long-term tube feeding formula must deliver not only the essential macro- and micronutrients, but other dietary constituents that may become conditionally essential or important for well-being. A short-term tube feeding patient would consume an oral diet before and after the tube feeding episode, thus limiting any negative effects caused by any missing conditionally essential compounds. Long-term, tube fed patients (often sedentary or bedridden), however, may suffer from any number of health complications for example, increased bone or muscle loss, low-grade inflammation, reduced gastrointestinal motility, increase resistance and depressed or altered immune systems. The nutritional needs of such long-term, tube fed patients with these types of chronic diseases will certainly differ from those requiring short-term tube feedings. Accordingly, Applicant has found that patients suffering from these processes associated with decreased activity, should be administered tube feed formulations having adequate calcium, vitamin D, and protein, complex carbohydrates, fiber (including prebiotics), nucleotides, ω-3 fatty acids, antioxidants, phytonutrients, and/or various herbs, spices and flavorings, or combinations thereof. Although the feeding needs of long-term tube feed patients is different than short-term tube feed patients, the skilled artisan will appreciate that the present compositions may be used for either short or long-term tube feed patients, as well as patients receiving supplemental nutritional.

Many patients on long-term tube feed formulations are older adults. Although the aging process is natural, there are a number of physiological changes that should be limited or slowed if possible. These physiological changes include, for example, sarcopenia (loss of lean body mass), increase risk of osteoporosis or fracture, depressed gut health, altered immune function, increase oxidative stress, increased insulin resistance and loss of appetite. Particularly in older adults, dysphagia, stroke head and neck cancer, and neurological cases including, but not limited to, Parkinson's Disease, Alzheimer's and other neurological changes associated with aging are common conditions that require tube feeding.

There are many similarities between elderly adult and sedentary adult populations. The nutritional compositions that are fed to these patients should address, among other conditions, musculoskeletal health, gut health, immune function, low grade inflammation, oxidative stress and insulin resistance. Applicant has identified several key nutrients to address the needs of adult patients who experience any or all of the physiological impacts listed above.

For example, adult patients experiencing a change in glucose metabolism, which includes, for example, insulin resistance and impaired glucose uptake, may be fed nutritional compositions that include ingredients such as, but not limited to, complex carbohydrates, fiber, herbs, spices, phytochemicals and/or flavorings such as ginseng or cinnamon. Likewise, adult patients experiencing a change in gut function may be fed nutritional compositions that include ingredients such as, but not limited to, fiber (both soluble and insoluble), prunes, nucleotides, prebiotics and probiotics.

Further, for adult patients experiencing hypercholesterolemia or hypertriglyceridemia or for prevention of related diseases, tube feed formulations or oral nutritional supplements (liquid or solid) may include, for example, ω-3 polyunsaturated fatty acids, monounsaturated fatty acids, phytochemicals, plant sterols/stanols, soluble fiber, and herbs, spices and/or flavorings including, for example, garlic or cinnamon. The saturated fatty acids, however, should be limited to less than 7% of the total energy, the cholesterol should be limited to less than 200 mg, and the trans fatty acids should also be limited.

Nutritional compositions including, for example, antioxidants, nucleotides, prebiotics and ω-3 polyunsaturated fatty acids may be fed to adult patients experiencing a decrease in immune function or an increase in oxidative stress.

Additionally, adult patients experiencing an impact on musculoskeletal health including, for example, bone health and muscle mass/strength, may be fed nutritional compositions having calcium, high amounts of vitamin D and high quality protein. A large bolus of protein may be administered at a given time to optimize protein synthesis in elderly individuals. See, Arnal M A, et al., *Protein pulse feeding improves protein retention in elderly women*, Am. J. Clin. Nutr., 69:1202-8 (1999); see also, Symons et al., *Aging does not impair the anabolic response to a protein-rich meal*, Am. J. Clin. Nutr., 86:451-6 (2007). Indeed, a bolus of 20-30 g protein is thought to optimally stimulate protein synthesis. Details of many of these conditions are discussed further below with respect to the nutritional needs of pediatric patients. In this way, the skilled artisan will appreciate that many nutrients required by adult patients may also be required by pediatric patients.

With respect to children, there are a few basic concepts that apply to most, if not all, pediatric or young adult patients. For example, these patients require adequate and appropriate nutrition to ensure proper growth. These patients would also benefit from measures to prevent chronic diseases. Indeed, preventative nutrition to reduce the risk of developing coronary vascular disease and cancer later in life may be particularly relevant for this population.

More specifically, there are conditions common to pediatric patients that may require long-term feedings (e.g., tube feedings). Several conditions include, but are not limited to, cystic fibrosis, quadriplegia, cerebral palsy and neuromuscular disorders. Applicant has also identified several key nutrients to address the needs of pediatric patients who experience any or all of the physiological impacts listed above.

To ensure adequate growth, pediatric patients must maintain adequate nutritional status (macro- and micronutrients), and be fed nutritional compositions that provide adequate energy.

Pediatric patients suffering from poor bone health, which includes, but is not limited to, osteopenia and osteoporosis, may be fed nutritional compositions having adequate or high amounts of calcium and vitamin D.

Gut health, including motility and microbiota composition (impacted by a variety of factors, including antibiotic usage), in pediatric patients may be improved by providing fiber (insoluble and soluble), prebiotic fibers and probiotics, and nucleotides.

Nutritional compositions having increased amounts of fat (e.g., 35-40% total energy), protein, and vitamins and minerals may be fed to patients suffering from pancreatic insufficiency and/or malabsorption of fat and fat soluble vitamins. Often times, a low-fat diet is recommended in patients with pancreatic insufficiency to reduce steatorrhea. Patients suffering from inflammation may be fed nutritional compositions including antioxidants, nucleotides, prebiotics and ω-3 polyunsaturated fatty acids.

In a more specific example, cerebral palsy is a chronic, non-progressive motor disability that results from an injury to the developing brain early in life. Cerebral palsy is generally characterized by dysfunctions in motor coordination and muscle tone. Because long-term tube fed pediatric patients are often wheel-chair bound or have severe difficulty with ambulation, their energy needs are significantly lower than those of healthy children, but their protein needs are often higher. Additionally, as described below, maintenance of bone health, prevention of pressure ulcers and maintenance of healthy immune function, gut health are common concerns. These children often require exclusive tube feeding.

Indeed, bone fractures are a significant problem in children with spastic quadriplegia due to many factors. Many children with cerebral palsy are taking anticonvulsant medications for seizure control, and alterations in vitamin D and calcium metabolism are associated with some anticonvulsant use. See, Hahn, T. J. et al., *Effect of Chronic Anticonvulsant Therapy on Serum 25-Hydroxycalciferol Levels in Adults*, The New England J. of Med., pp. 900-904 (1972). See also, Hunter, J. et al., *Altered Calcium Metabolism in Epileptic Children on Anticonvulsants*, British Medical Journal, pp. 202-204 (1971). See also, Hahn, T. J. et al., *Phenobarbital-Induced Alterations in Vitamin D Metabolism*, J. of Clinical Investigation, Vol. 51, pp 741-748 (1972). Although the influence of anticonvulsant medication on vitamin D status is not completely clear, it is apparent that non-ambulatory children are at increased risk for bone fractures.

Studies have shown that medications to control seizures, such as phenobarbital and Dilantin, can alter the metabolism and the circulating half-life of vitamin D. Research has also suggested that patients on at least two anti-seizure medications who are institutionalized and, therefore, not obtaining most of their vitamin D requirement from exposure to sunlight, increase their vitamin D intake to approximately 25 μg (1,000 IU)/day to maintain their serum 25(OH)D levels within the mid-normal range of 25 to 45 ng/ml (62.5 to 112.5 nmol/liter). It is thought that this should prevent the osteomalacia and vitamin D deficiency associated with anti-seizure medications. Applicant has found that pediatric patients suffering from such bone health/anticonvulsant issues may see improvement in these areas if administered nutritional compositions having increased amounts of calcium and vitamin D.

In yet another example, patients, and especially children, with cerebral palsy and neuromuscular disorders are also frequently at risk of developing pressure ulcers or chronic wounds and, as such, may require special diets. Individuals that are susceptible to chronic wounds include, for example, those with prolonged immobilization, bed and chair bound and/or experiencing incontinence, those that are experiencing protein-energy malnourishment, those with neurological, traumatic or terminal illnesses, or those with circulatory or sensory deficits. See, Agency for Health Care Policy and Research, 1992, 1994. Receiving adequate nutrition plays a key role in prevention and treatment of such chronic wounds.

For example, specific nutrients including protein, vitamin A, vitamin C, vitamin E, zinc, arginine, citrulline and glutamine can play a role in reducing the risk of developing pressure ulcers, particularly if a deficiency is suspected. Adequate hydration also plays a significant role in reducing the risk of developing pressure ulcers. Indeed, it has been reported that incidence of pressure ulcer development was lower in a group receiving additional protein, arginine, vitamin C and zinc when compared to a control group (13% versus 72%). See, Neander, et al., *A specific nutritional supplement reduces incidence of pressure ulcers in elderly people*, Numico Research, www.numico-research.com.

Once a chronic wound or pressure ulcer has developed, various nutrients play an important role in healing, with specific nutrients having an impact at different phases of the process. For example, Table 1 below demonstrates the key nutrients that impact different phases of wound healing. As is shown in Table 1, certain vitamins, minerals and amino acids should be present at the different phases of wound healing.

TABLE 1

| Phase | Process | Key Nutrients |
|---|---|---|
| Phase I: Inflammation | Wound exudation Fibrin clot formation | Vitamin C Vitamin E Selenium Arginine Cysteine Methionine |
| Phase II: Proliferation | Angiogenesis Fibroblast proliferation Collagen synthesis Wound matrix formation and epithelialization | Vitamin A Vitamin C Thiamin Pantothenic acid Zinc Manganese |
| Phase III: Maturation and Remodeling | Collagen cross linkage Wound contraction Tensile strength development | Vitamin A Vitamin C Zinc Copper Manganese |

Applicant has surprisingly found that pediatric patients suffering from pressure ulcers may see improvement in these areas if administered nutritional compositions having increase amounts of protein, vitamin A, vitamin C, vitamin E, zinc, arginine, citrulline and glutamine.

There are also significant health economic implications with prevention of pressure ulcer development or progression. For example, the average healing times for pressure ulcers are longer at later stages of the ulcers, with Stage III and Stage IV ulcers requiring substantially longer treatment than Stage II. In a UK cost of illness study, it is clear that there are increased treatment costs with increased severity of pressure ulcers. See, Bennett G, et al., *The cost of pressure ulcers in the UK*, Age and Ageing, 33: 230-235 (2004). In another study, it was shown that Stage III and Stage IV pressure ulcers cost substantially more to treat than Stage II pressure ulcers. See, Xakellis G C, et al., *The cost of healing pressure ulcers across multiple health care settings*, Adv. Wound Care, 9:18-22 (1996). These significant costs are shown below in Table 2.

TABLE 2

| Stage | Total Treatment Cost per Pressure Ulcer Including Hospital Stay Mean (SD) | Treatment Cost per Pressure Ulcer Excluding Hospital Stay Mean (SD) | Hospitalization Cost per Pressure Ulcer |
|---|---|---|---|
| Stage I (n = 37) | $1,119 (4,234) | $443 (581) | $676 |
| Stage III and IV (n = 8) | $10,185 (27,635) | $700 (831) | $9,485 |
| All ulcers (n = 45) | $2731 (12,184) | $489 (629) | $2,242 |

In another example, central adiposity has been associated with insulin resistance and low grade inflammation, thus is it possible that provision of low energy, high protein diets to growing children with low physical activity will prevent the insulin resistance thus permitting more effective insulin activity and thus anabolism. High protein diets have been shown to modulate secretion of anabolic hormones such as growth hormone. See, Clarke, et al., *Effect of high protein-feed supplements on concentrations of growth hormone ("GH"), insulin-like growth factor-I ("IGF-I") and IGF-binding protein-3 in plasma and on the amounts of GH and messenger RNA for GH in the pituitary glands of adult rams*, J. Endocrinol. 138 (3):421-427 (1993). See, also, J. R. Hunt, et al., *Dietary protein and calcium interact to influence calcium retention: a controlled feeding study*, Am. J. Clin. Nutr. 89 (5):1357-1365 (2009). See, also, G. Blanchard, et al., *Rapid weight loss with a high-protein low-energy diet allows the recovery of ideal body composition and insulin sensitivity in obese dogs*, J. Nutr. 134 (8 Suppl):21485-21505 (2004).

These benefits are particularly important during rapid growth as the growth hormone axis has been shown to be associated with chronic diseases later in life. Therefore modulation of the growth hormone axis (including IGF-1) will benefit the clinical outcome of the patient both in the short term and also in later years. This can lead to significant improvement in quality of life but also in positive health economic outcomes. See, J. M. Kerver, et al., *Dietary predictors of the insulin-like growth factor system in adolescent females: results from the Dietary Intervention Study in Children (DISC)*, Am. J. Clin. Nutr. 91 (3):643-650 (2010).

In another example, hospitalized, institutionalized, and recovering patients may be at an increased risk of metabolic disturbances caused by poor renal and/or pulmonary function. While the body's blood pH is fairly well maintained over time, primarily through regulation by the kidneys and lungs, dietary intake can significantly influence the body's acid/base balance. As a result, the acid-base potential of the diet becomes increasingly important in maintenance of the patient's health, including musculoskeletal and immune health.

Upon ingestion and after metabolism, foods can be categorized as either more acidic or more alkaline producing. Correlational human intake data suggests that diets higher in fruits and vegetables support a net alkaline environment to help maintain metabolic homeostasis. Conversely, acid producing diets have been found to negatively impact musculoskeletal health. Correction of low-grade metabolic acidosis through diet modification may help to preserve skeletal muscle mass and improve the health of patients with a variety of pathological conditions including, for example, muscle loss.

Because long-term tube fed pediatric patients, for example, lack variation in their food sources they may be particularly susceptible to the effects of such acid-forming diets. Although the kidneys are efficient at neutralizing acids, long term exposure to high acid is believed to overwhelm the kidneys' capacity to neutralize acid and potential damage may occur. As a result, alkaline compounds that include, but are not limited to, calcium are used to neutralize these dietary acids (in the case of muscle, glutamine can act as a buffer). The most readily available source of calcium in the body is bone. One theory is that high acid diets may contribute to bone loss as the body mobilizes stored calcium to buffer metabolic acid. The hypothesis is that low acid diets may result in benefits that include attenuation of bone and muscle loss as well as maintaining renal health. See, Wachman, A., et al., *Diet and Osteoporosis*, Lancet, 1:958-959 (1968); see also, Frassetto L, et al., *Potassium Bicarbonate Reduces Urinary Nitrogen Excretion in Postmenopausal Women*, J. Clin. Endocrinol. Metab., 82:254-259 (1997).

In addition to bone specific effects, human correlational data suggests that dietary intake of fruits and vegetables support a net alkaline environment which can help regulate metabolic homeostatis. This net alkaline state has been associated with an enhanced preservation of lean body mass, at least in older individuals. See, Dawson-Hughes B, et al., *Alkaline diets favor lean tissue mass in older adults*, Am. J. Clin. Nutr., March; 87(3):662-5 (2008). Thus, the manipulation of Phosphorus (P), Sodium (Na), Magnesium (Mg), Potassium (K) and Calcium (Ca) in complete nutritional formulas can serve to enhance net alkaline production to further minimize endogenous skeletal muscle proteolysis as well as preserve lean body mass. The same is true of the manipulation of a protein source.

In an embodiment, the nutritional compositions of the present disclosure may be administered as a bolus or a continuous tube feeding. In an embodiment, the tube feedings are administered as a bolus since it maximizes the physiological response to the feeding occasion. This method provides complete nutrition to patients in that a concentrated dose of protein is delivered at each feeding. This concentrated provision of protein is essential to increasing plasma amino acids (e.g., leucine), stimulating protein synthesis, and attaining a net positive protein balance. This anabolic state post-feeding is required to optimize growth through the accrual of lean body mass and linear bone growth (accrual of bone mineral density). The mechanism is related to the above mentioned increase in serum leucine as well as anabolic endocrine response including the stimulation of the insulin-IGF-1-GH axis leading to increased uptake and bio-utilization of substrates for musculoskeletal development (thus, leading to reduced accumulation of visceral adiposity).

The present disclosure is directed to nutritional products and compositions that provide patients requiring tube feedings and/or oral nutritional supplements with sufficient levels of certain micronutrients and macronutrients and that mimic a healthy, whole food diet and provide physiological benefits and emotional appeal. In order to mimic a "whole food" diet, the formulas of the present disclosure may, for example, increase the number and variety of fruits and vegetables, increase the variety of macronutrient sources and include other components found in whole foods including, for example, nucleotides, phytonutrients, herbs, spices or flavorings, plant sterols, etc.

One manner in which tube feeding formulas can mimic healthy, whole food diets is to increase the servings of fruits and vegetables administered per day. Indeed, any incremental increase in fruit and vegetable content as compared to current market tube feed formulations would be beneficial to a tube fed patient or patient requiring oral nutritional supplements. From a review of 200 epidemiological studies, increase intakes of fruits and vegetables reduced the risk of several types of cancers. See, Block et al., *Fruit, vegetables and cancer prevention: A review of the epidemiological evidence*, Nutrition and Cancer, 18: 1-29 (1992). Further, for every one serving per day increase in fruits or vegetables, there was a 4% reduction in coronary heart disease risk. See, Joshipura et al., *The effect of fruit and vegetable intake on risk for coronary heart disease*, Ann. Intern. Med. 134:1106-1114 (2001). In addition, other studies have shown benefits of flavonoid consumption and reduced risk of death from coronary heart disease. The major sources of flavonoids included teas, apples, and onions. See, Hertog et al., *Dietary antioxidant flavonoids and risk of coronary heart disease: the Zutphen Elderly Study*, The Lancet, vol. 342, Issue 8878:1007-1011 (1993).

Applicant has found that providing at least 5 servings or at least 400 g of fruits and vegetables per complete feeding provides the tube fed patient with amounts of fruits and vegetables typically recommended to individuals consuming an oral, whole food diet. In an embodiment, at least 6 or 7 servings of fruits and vegetables are provided in the present nutritional compositions. In yet another embodiment, at least 8 servings of fruits and vegetables are provided in the present nutritional compositions. In an embodiment, the fruits and vegetable reduce the risk of several chronic diseases.

As such, in an embodiment, nutritional compositions of the present disclosure include a whole food, or a real food, component. Whole foods contain beneficial food constituents in addition to the well-recognized macronutrients, vitamins and minerals. Several of these food constituents include phytochemicals and nucleotides, which provide several benefits to a patient on a long-term tube feeding diet, or requiring oral nutritional supplements, as will be further discussed below.

For example, phytonutrients can act as antioxidants within the body. See, Carlson et al., *The total antioxidant content of more than 3100 foods, beverages, spices, herbs and supplements used worldwide*, Nutr. J., 9:3 (2010). Thus, it is beneficial to provide phytonutrients in certain amounts. For example, in a 2008 report, it was estimated that if an individual consumed 5 servings of fruits and/or vegetables daily, polyphenol intake would be greater than 500 mg, and probably closer to 500-1,000 mg if cocoa, tea or coffee is consumed. See, Williamson, et al., *Dietary reference intake (DRI) value for dietary polyphenols: are we headed in the right direction?*, British Journal of Nutrition, 99, Suppl. 3, S55-59 (2008).

In a study including Finnish adults (n=2007), mean total intake of polyphenols (phenolic acids, anthocyanidins, and other flavonoids, proanthocyanidins, and ellagitannins) was 863±415 mg/d; intakes of specific classes included 641 mg/d phenolic acids, 128 mg/d total proanthocyanidins, 47 mg/d anthocyanidins, 33 mg/d total flavonoids, 12 mg/d ellagitannins, 309 mg/d isoflavones, 0.9 mg/d lignans, 5.9 mg/d carotenoids, and 368 mg/d sterols. The largest contributors to phenolic acid intake was coffee followed by breads and tea; berries and berry products to anthocyanins; fruits and tea to flavonols, flavonones and flavones; apples, berries, tea and chocolate to proanthocyanidins; vegetables to carotenoids; soy products to isoflavonoids; and seeds, soy products, rye and cereal products to lignans. See, Ovaskainen et al., *Dietary Intake and Major Food Sources of Polyphenols in Finnish Adults*, American Society for Nutrition J. Nutr.

138:562-566 (March 2008). This information is, however, an example and is not necessarily representative of worldwide intake as it may vary depending on food patterns and preferences. In a another study near Indianapolis involving 280 people, average intakes of lutein and zeaxanthin, and β-carotene, were 1101±838 and 2935±2698 μg/d, respectively. See, Curran-Celentano et al., *Relation between dietary intake, serum concentrations, and retinal concentrations of lutein and zeaxanthin in adults in a Midwest population*, American Journal of Clinical Nutrition, Vol. 74, No. 6, 796-802 (December 2001).

It is possible to estimate phytonutrient content to foods by using the USDA Standard Reference database (Release 23). This database contains, for example, data on carotenoid content in foods. Examples of such carotenoid contents include: (i) 1 cup chopped, raw carrots (NDB No: 11124), beta carotene 10605 mcg, alpha carotene 4451 mcg, lycopene 1 mcg, lutein+zeaxanthin 328 mcg; (ii) 1 cup spinach (NDB No: 11457): beta carotene 1688 mcg, lutein+zeaxanthin 3659 mcg; (iii) 1 cup tomatoes, red, ripe, cooked (NDB No: 11530): beta carotene 703 mcg, lycopene 7298 mcg, lutein+zeaxanthin 226 mcg; (iv) 1 cup chopped broccoli, raw (NDB No: 11090): beta carotene 329 mcg, alpha carotene 23 mcg, beta cryptoxanthin 1 mcg, lutein+zeaxanthin 1277 mcg; (v) 1 cup broccoli, frozen, chopped, cooked, boiled, drained, without salt (NDB No: 11093): beta carotene 1098 mcg, alpha carotene 35 mcg, beta cryptoxanthin 2 mcg, lutein+zeaxanthin 2015 mcg; (vi) 1 cup blueberries, raw (NDB No: 09050): beta carotene 47 mcg, lutein+zeaxanthin 118 mcg; (vii) 1 cup halves, strawberries, raw (NDB No: 09316): beta carotene 11 mcg, lutein+zeaxanthin 40 mcg; and (viii) 1 cup slices apple, raw with skin (NDB No: 09003) beta carotene 29 mcg, beta cryptoxanthin 12 mcg lutein+zeaxanthin 32 mcg.

The phytonutrient content of foods, however, may vary depending on processing, growing conditions, cultivar, etc. See, Kim H J et al., *Changes in Phytonutrient Stability and Food Functionality during Cooking and Processing*, Korean J Food Cookery Sci., Vol 22 No 3: 402-417 (2006). Since processing and handling can influence the phytonutrient content of the final product, the present disclosure relates to a tube feed that contains fruit and vegetable ingredients with known/standardized levels of select phytonutrients, and are processed in such a manner to maintain a desired level of phytonutrients in the end product.

There are many factors that may impact the phytonutrient content of various fruits and vegetables. For example, physical factors may include, but are not limited to, temperature, pressure, oxidation/reduction potential, pH, enzymes, metals, leaching, light, water activity, etc. Biological factors affecting food constituents may include, but are not limited to, maturity, cultivar, state of the tissue, composition, etc. See, Kalk, *Effects of Production and Processing Factors on Major Fruit and Vegetable Antioxidants*, Journal of Food Science, Vol 70, Nr 1 (2005); see, also, Kim H J, et al., *Changes in Phytonutrient Stability and Food Functionality during Cooking and Processing*, Korean J Food Cookery Sci., Vol 22 No 3: 402-417 (2006). Depending on the phytonutrient/fruit or vegetable, processing may destroy or enhance presence and/or bioavailability. Additionally, Kalk reports that carotenoids are relatively stable through processing, while phenolic antioxidants are more prone to losses. See, Kalk, Table 3.

Furthermore, the impact of processing on tomatoes phytonutrient levels has been well studied, such that thermal processing increases the bioavailable content of lycopene. See, Dewanto et al., *Thermal Processing Enhances the Nutritional Value of Tomatoes by Increasing Total Antioxidant Activity*, J. Agric. Food Chem., 50 (10), pp 3010-3014 (2002). On the other hand, thermal processing of other fruits and vegetables may degrade these components. Severe heat treatment of red cabbage (e.g., canning) resulted in 73% degradation of glucosinolates. See, Oerlemans et al., *Thermal degradation of glucosinolates in red cabbage*, Food Chemistry, 95; 19-29 (2006). Similar results were found during cooking of broccoli (74% loss after microwaving). See, Vallejo, F. et al., *Glucosinolates and vitamin C content in edible parts of Broccoli florets after domestic cooking*, European Food Research and Technology, 215, 310-316 (2002).

Another manner in which nutritional compositions can mimic healthy, whole food diets is to increase the variety of food consumed per day. For example, with respect to macronutrients, it is important that nutritional compositions include a variety protein, fat and carbohydrate sources. Indeed, formulations having a variety of protein, fat and carbohydrate sources more closely resemble a whole food diet. With respect to micronutrients, the source of vitamins and minerals includes at least two sources or forms of a particular nutrient.

The present nutritional compositions may include at least 4 different sources of macronutrients, which include, for example, protein, fat, and carbohydrates. In another embodiment there may be at least 5, 6, 7, or 8 different sources of macronutrients. In an embodiment, there exists at least one source each of protein, fat and carbohydrates in the nutritional compositions. However, the skilled artisan will appreciate that there may be any combination of the at least 8 different sources of macronutrients. For example, there may be 3 or more protein sources in the present nutritional compositions. In an embodiment, there may be 3 or more carbohydrate sources in the nutritional compositions. In another embodiment, there may be at least 3 or more fat sources in the nutritional compositions. Alternatively there may be 4 or more of the protein, carbohydrate, fat or fiber sources in the composition. The sources may be the same source, or a different source. In another embodiment, there may be at least 3 or more fiber sources in the nutritional compositions.

In an embodiment, vegetable proteins may be included to further enhance the net alkaline profile of the formula while delivering high quality protein blends that provide the essential nutritional requirements for supporting growth and development. Based on the nutritional profile of specific vegetable proteins (e.g., pea protein isolate) there are limitations in the amount of vegetable protein sources that can be included in a formula. For example, the amino acid profile of pea protein includes all of the indispensable amino acids. Pea protein is relatively rich in arginine, but limiting in the sulphur-containing amino acids, methionine, and cysteine. However, it is possible, for example, to blend pea protein isolates with a complete protein source (such as milk protein or complete vegetable proteins) having sufficient sulphur-containing amino acids to offset such deficiency. Canola protein (i.e., isolates, hydrosylates and concentrates) is one such vegetable protein which can provide appreciable amounts of sulfur-containing amino acids to further augment the amino acid profile to deliver the necessary protein quality to the patient. Additionally, animal derived proteins are typically more abundant in sulphur-containing amino acids than vegetable proteins. Furthermore, given the potential for viscosity limitations associated with, for example, tube feeding and the need to maintain the necessary nutritional value of protein, the formula may include about 10-50% protein coming from a vegetable source.

The present compositions may also use a mixture of macronutrient sources that have associated health benefits and/or emotional appeal. For example, the protein may be derived from vegetable sources while maintaining high Protein Digestibility Corrected Amino Acid Scores ("PD-CAAS"). The fat sources may include olive and canola oil, and may be less refined to maintain higher polyphenol content.

The skilled artisan will appreciate that the protein content of the present nutritional compositions may be higher than typical long-term tube feed formulations in embodiments having high amounts of protein. For example, the Recommended Dietary Allowance ("RDA") of protein for both men and women is 0.80 g of good quality protein/kg body weight/day and is based on careful analysis of available nitrogen balance studies. See, National Academy of Sciences, Institute of Medicine, Food and Nutrition Board, *Dietary Reference Intakes for Energy, Carbohydrate, Fiber, Fat, Fatty Acids, Cholesterol, Protein, and Amino Acids* (*Macronutrients*), Chapter 10 (2005). In an embodiment, the present compositions provide protein to a patient in an amount of from about 1.0 to 2.5 g/kg body weight/day. In another embodiment, the present compositions provide protein to a patient in an amount of about 1.5 to 2.0 g/kg body weight/day. Accordingly, the present compositions may provide protein to a patient in an amount that is nearly twice the RDA of protein for men and women.

In another embodiment, the protein is provided in an amount to provide about 5 to about 40% energy from protein per day. In another embodiment, the protein is provided in an amount to provide from about 10% to about 35% energy from protein per day. In another embodiment, the protein is provided in an amount to provide from about 25% to about 30% energy from protein per day.

Sources of complex carbohydrates or whole grains such as, for example, bran, oatmeal, barley, beans, rice, and peas, may be used in the present compositions, as recommended in the Dietary Guidelines of the Dietary Guidelines Advisory Committee. Any suitable carbohydrate may be used in the present nutritional compositions including, but not limited to, sucrose, lactose, glucose, fructose, corn syrup solids, maltodextrin, modified starch, amylose starch, tapioca starch, corn starch or combinations thereof. Carbohydrates may be provided in an amount sufficient to provide from about 40% to about 70% total energy. In an embodiment, the carbohydrates are provided in an amount sufficient to provide from about 45% to about 65% total energy of the nutritional compositions.

A source of fat may also be included in the present nutritional compositions. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like), animal fats (such as milk fat, tallow, lard, poultry fat, fish oil, etc.), or combinations thereof. Additionally, fats such as olive oil and canola oil may be used in the present compositions and are commonly purported to have heart health benefits. Fats may be provided in an amount sufficient to provide from about 20% to about 40% total energy. In an embodiment, the fats are provided in an amount sufficient to provide from about 25% to about 35% total energy of the nutritional compositions.

With respect to fruits and vegetables, the present compositions may increase the variety of foods consumed per day by combining and using several different types of fruits and vegetables. The nutritional compositions of the present disclosure may provide fruits and vegetables in an amount recommended by individuals consuming a whole food diet. In one embodiment, the effective amount is at least about 3 servings of fruits and vegetables. In an embodiment, the nutritional compositions include from about 4 to about 10 servings of fruits and vegetables. In an embodiment, the nutritional compositions include at least about 6 or 7 servings of fruits and vegetables. In an embodiment, any incremental amount of fruits and vegetables is beneficial.

Fruits included in the present nutritional compositions may include any known fruit such as, but not limited to, apples, bananas, coconut, pear, apricot, peach, nectarines, plum, cherry, blackberry, raspberry, mulberry, strawberry, cranberry, blueberry, grapes, prunes, grapefruit, kiwi, rhubarb, papaya, melon, watermelon, pomegranate, lemon, lime, mandarin, orange, tangerine, guava, mango, pineapple, etc. Similarly, vegetables may include any known vegetable such as, but not limited to, amaranth, arugula, brussels sprouts, cabbage, celery lettuce, radicchio, water cress, spinach, pumpkin, squash, mushrooms, peas, beans, beets, carrots, potatoes, radish, rutabaga, turnips, etc.

It is also possible to include fruits and vegetables from the five different colors categories, which represent a variety in the types of phytochemicals provided in the formulation. See, Heber D, et al., *Applying Science to Changing Dietary Patterns*, J. Nutr, 131:3078 S-3081S (2001). Phytochemicals are non-nutritive compounds that are found in many fruits and vegetables, among other foods. There are thousands of phytochemicals that can be categorized as flavonoids and allied phenolic and polyphenolic compounds, terpenoids, e.g., carotenoids and plant sterols, or alkaloids and sulfur containing compounds.

With respect to the color groups of fruits and vegetables, the present compositions may include at least one fruit/vegetable from each of the colors green, blue/purple, red, orange and white. Green fruits/vegetables include, for example, spinach, broccoli, peas, beans and kiwi. Blue/purple fruits/vegetables include, for example, grapes, blueberries and eggplant. Red fruits/vegetables include, for example, raspberries, cranberries and tomatoes. Orange fruits/vegetables include, for example, carrots, mangoes, pumpkin, oranges and squash. White fruits/vegetables include, for example, cauliflower, onion and banana. Accordingly, it is possible to diversify the nutrient and phytonutrient content by including fruits and vegetables from all color groups. The skilled artisan will appreciate that this list is not exhausted and that other colored fruits/vegetables may be used in addition to those listed above. The skilled artisan will appreciate that any known fruits and vegetables may be used in the present nutritional compositions. Further, the skilled artisan will also appreciate that the fruits and/or vegetables may be provided in any amounts effective to achieve the advantages described above.

Phytochemicals are active in the body and, in general, act similarly to antioxidants. They also appear to play beneficial roles in inflammatory processes, clot formation, asthma, and diabetes. Researchers have theorized that to receive the most benefit from consumption of phytochemicals, they should be consumed as part of whole foods, because of the complex, natural combination and potentially synergistic effects. See, Liu R H., *Health benefits of fruit and vegetables are from additive and synergistic combinations of phytochemicals*, Am. J. Clin. Nutr., 78:517 S-520S (2003). This may partially explain the health benefits associated with consumption of whole fruits and vegetables. Increased intake of fruits and vegetables is associated with reduced risk of many chronic diseases. In order to enhance the phytochemical profile of the present nutritional compositions, in an embodiment, the compositions include various fruits and vegetables containing these compounds.

Another manner in which tube feeding formulas can mimic healthy, whole food diets is to include food components that are typically present in a healthy, whole food diet. To this end, the present compositions may have added spices, herbs or flavorings with purposed health benefits such as, for example, antioxidant activity, or that provide emotional appeal for certain populations. For example, the present compositions may include garlic and/or cinnamon to reduce cholesterol and lower blood pressure, ginseng and cinnamon for glycemic control, tumeric, curcumin, basil, rosemary, mint and lemon grass for anti-carcinogenic properties, ginger for arthritic pain, ginkgo biloba and ginseng for cognitive function, curcumin and ginger for anti-inflammatory properties, ginger for an anti-nausea, and herbs for improving general health conditions.

Variety in food and tastes may maintain the various taste receptors in the gut. Increased variety of foods and/or food components and flavors may be delivered to stimulate specific taste receptors in the gut, thus eliciting different physiological responses. For example, umami receptors have been identified in the gastrointestinal tract, which sense the presence of savory flavors (mushrooms, seafood, fermented soy flavorings, or common flavor enhancers such as monosodium glutamate ("MSG") and/or inosine-5'-monophosphate ("IMP")). Animal data has shown that the addition of MSG and/or IMP to diets improves the secretion of mucus and protection of the small bowel. In an embodiment, mushrooms and fermented soy flavorings may be added to the present compositions because mushrooms and fermented soy flavorings such as, for example, soy sauce, contain the highest naturally occurring levels of these compounds and could be useful as ingredients in tube feed formulations for support of the gastrointestinal tract. In this manner, umami receptor activation may have dual benefits in glucose metabolism (increase GLP-1 release) and in duodenal mucosal protection and regeneration due to GLP-2 release from L cells. See, Nakamura E, et al., *Physiological roles of dietary free glutamate in gastrointestinal functions*, Biol. Pharm. Bull., 31, 10:1841-1843 (2008); Kojo A, et al., *Effects of glutamate, the "umami" substance, on development and healing of NSAID-induced small intestinal lesions in rats*, Abstract presented at Digestive Disease Week 2010 (W1345); Wang J, et al., *Umami receptor activation increases duodenal bicarbonate secretion via GLP-2 release in rats*, Abstract presented at Digestive Disease Week 2010 (W1719).

Also, stimulation of other taste receptors has been shown to have effects in animal or cell culture studies. For example, stimulation of bitter taste receptor in the gut increases CCK release and delays gastric emptying. See, Chen M C, et al., *Bitter stimuli induce Ca2 signaling and CCK release in enteroendocrine STC-1 cells: role of L-type voltage-sensitive Ca2 channels*, Am. J. Physiol. Cell Physiol. 291, C726-C739 (2006); Jang H J, et al., *Gut expressed gustacin and taste receptors regulate secretion of glucagon-like peptide 1.*, Proc. Natl. Acad. USA 104:15069-74 (2007); Margolskee R F, et al., *T1R3 and gustducin in gut sense sugars to regulate expression of Na-glucose cotransporter 1.*, Proc. Natl. Acad. USA 104:15075-80 (2007); Mace O J, et al., *Sweet taste receptors in rat small intestine stimulate glucose*, J. Physiol. 582.1, pp 379-392 (2007).

In an embodiment, the present compositions include plant sterols for heart health to reduce absorption of cholesterol in the gut. Phytosterols (also called plant sterols) are a group of steroid alcohols that naturally occur in plants. Phytosterols occur naturally in small quantities in vegetable oils, especially sea buckthorn oil, corn oil, and soybean oil. One example of a phytosterol complex, isolated from vegetable oil, is cholestatin, composed of campesterol, stigmasterol, and brassicasterol. The skilled artisan will appreciate that any known phytosterols may be used herein. In an embodiment, up to about 5 g of plant sterols may be added to the present compositions per complete feed. In an embodiment, about 1 to about 4 g of plant sterols may be added to the present compositions. In another embodiment, about 2 g of plant sterols are added to the present compositions per complete feed. In this manner, plant sterols may be beneficial in compositions containing cholesterol, or an oral nutritional supplement in which the consumer is consuming other food items containing cholesterol. In another embodiment, however, some long-term tube-fed patients receive very little amounts of exogenous cholesterol. In this case, the present compositions may not include sterols that may hamper cholesterol.

As discussed above, nucleotides are food constituents found in several types of food including red meats, organ meats, poultry, fish, shellfish, lentils, beans, asparagus and fermented beverages, among others. Although endogenous synthesis constitutes a major source of nucleotides, nucleotides can also be obtained in the form of nucleoproteins naturally present in all foods of animal and vegetable origin including, for example, animal protein, peas, yeast, beans and milk. Further, concentrations of RNA and DNA in foods are dependent on cell density. Thus, meat, fish and seeds have higher nucleotide content than milk, eggs and fruits. Consequently, organ meats, fresh seafood, and dried legumes are rich food sources. Endogenous synthesis of nucleotides, although a high energy requiring process, appears to be sufficient in healthy individuals. However, the need for exogenous (dietary source) nucleotides occurs during situations of growth or stress, e.g., gut injury, sepsis, and immune challenge. See, Kulkarni et al., *The Role of Dietary Sources of Nucleotides in Immune Function: A Review*, J. Nutr., vol. 124 pp. 1442S-1446S (1994). Therefore, several segments of the population on long-term tube feeds (elderly, pediatric populations, sedentary, bedridden and those with wounds), or patients requiring oral nutritional supplements, may particularly benefit from exogenous nucleotides.

The skilled artisan will appreciate that although endogenous synthesis constitutes a major source of nucleotides, nucleotides can also be obtained in the form of nucleoproteins naturally present in all foods of animal and vegetable origin including, for example, animal proteins, peas, yeast, beans, milk, etc.

The cell energy charge has been proposed as an important control for the cell to favor either anabolic or catabolic processes. Cell energy charge is defined Energy charge=(ATP+½ ADP)/(ATP+ADP+AMP), where ATP, ADP, and AMP signify adenosine 5'-triphosphate, -diphosphate, and -monophosphate, respectively. Metabolic stress, nutritional stress, or both may result in a loss of nucleotides from the adenylate pool and become conditionally essential under these conditions. The maintenance of the cell energy charge can attenuate the upregulation of catabolic processes resulting from metabolic stress, nutritional stress, or both, which includes protein breakdown.

AMP Protein Kinase ("AMPK") is a protein that serves as a cell energy charge sensor that responds to ATP/AMP as well phosphocreatine/creatine ("PCr"/"Cr") changing ratios for the prioritization of cellular processes based on available energy. Specifically, AMPK can target the translational control of skeletal muscle protein synthesis as well as upregulate the ubiquitin proteosome pathway.

Additionally, nucleotides can be beneficial in the nutritional management of pressure ulcer by improving the resistance to infection at the wound site. Chronic nucleotide supplementation may counteract the hormonal response associated with physiological stress, resulting in an enhanced immune response.

Extensive experimentation on the influence of dietary nucleotides on lymphocyte function and cellular immunity in rodent models has also been conducted. Evidence exists to assert that the absence of dietary nucleotides does significantly decrease specific and non-specific immune responses. Findings include decreased maturation and proliferation of lymphoid cells in response to mitogens, decreased resistance to bacterial and fungal infection, and increased allograft survival.

Lymphocyte differentiation and proliferation can be stimulated by specific nucleosides and, in turn, nucleotide metabolism may be influenced by stages of lymphocyte activation and function. Furthermore, de novo synthesis and salvage of purines and pyrimidines is increased in stimulated lymphocytes. In support, an established marker for undifferentiated T-cells, terminal deoxynucleotidyl transferase ("TdT"), has been identified in undifferentiated bone marrow and thymocytes of rodents fed diets devoid of nucleotides.

In vitro and in vivo studies of rodents on nucleotide free diets have demonstrated suppressed cell-mediated immune responses. Splenic lymphocytes from nucleotide free hosts evidenced significant decreases in proliferate response to mitogens, decreased interleukin-2 ("IL-2") production and lower levels of IL-2 receptor and Lyt-1 surface markers. IL-2 is a growth factor for lymphocytes, while Lyt-1 is a marker of helper-inducer T-cell immunity. Delayed cutaneous hypersensitivity was also lower.

These responses were largely reversed with additions of RNA or uracil, suggesting a formidable role for pyrimidines and/or limited capacity for their salvage. Furthermore, dietary nucleotides were shown to reverse lost immune response secondary to protein-calorie malnutrition more so than calories and protein alone. However, this reversal was limited to pyrimidines.

Investigations of the role of nucleotides in bacterial and fungal infection have also revealed increased resistance. Rodents on nucleotide containing diets demonstrated significant resistance to intravenous challenge of *Staphylococcus aureus* compared to those on nucleotide free diets. A decreased ability to phygocytose *S. aureus* was observed. Moreover, decreased survival times were observed in rodents on a nucleotide free diet after similar challenge with *Candida albicans*. Additions of RNA or uracil, but not adenine were shown to increase survival time.

The immunosuppressive effects of nucleotide free diets have also produced prolonged cardiac allograft survival in rodents as well as synergistic immunosuppression with cyclosporine A. These findings evidence influence on T-helper cell numbers and function. Various mechanisms of action have been proposed to explain these findings. Restriction of exogenous nucleotides is believed to influence the initial phase of antigen processing and lymphocyte proliferation via action on the T-helper-inducer as evidenced by increased levels of TdT in primary lymphoid organs. This is also suggestive of suppression of uncommitted T-lymphocyte response. Also, nucleotide restriction may cause arrest of T lymphocytes in the G phase of the cell cycle, thus inhibiting transition of lymphocytes to the S phase to illicit necessary immunological signals. Nucleotide restriction may also lower the cytolytic activity of natural killer ("NK") cells and lower macrophage activity.

Dietary nucleotides may also modulate T-helper cell mediated antibody production. A review of studies investigating nucleotide actions on humoral immune response identified effects in in vitro and in vivo animal models as well as in vitro actions in human systems. In vitro findings in splenic rodent cells primed with T-cell-dependent antigens displayed significant increases in the number of antibody producing cells in yeast RNA containing cultures. RNA additions to normal strains demonstrated similar results and were nullified by T-cell depletion. Thus, the antibody did not increase in response to T-cell independent antigens or polyclonal B cell activation. The specific antibody response of yeast RNA was attributed to nucleotides.

Immunoglobulin production has also been shown to increase in in vitro adult human peripheral blood mononuclear cell in response to T-cell dependent antigen and stimuli. Specifically, this involved increased immunoglobulin M ("IgM") and G ("IgG") production. IgM production increased in the functionally immature umbilical cord mononuclear cells in response to T-cell dependent stimuli as well.

Accordingly, in a state of nucleotide deficiency, incorporated dietary nucleotides could potentially exert similar immune effects in vivo. Antibody response to T-cell dependent antigen was suppressed in rodents maintained on nucleotide free diets for prolonged periods, and immune function was rapidly restored with nucleotide supplementation. However, the mixture used for supplementation showed no effect on in vitro antibody production to antigen-dependent antigens suggestive of nucleotide effects on local, specific immune response. In addition, significant increases in the numbers of antigen-specific immunoglobulin-secreting cells were observed in rodent splenic cells in the presence of nucleotides. Additions of AMP, GMP or UMP have also resulted in increased IgG response in rodents. GMP was also shown to increase IgM response. Studies in preterm infants on nucleotide supplemented formulas have revealed increased circulating levels of IgM and IgA in the first three months of life as well as higher concentrations of specific IgG against α-casein and β-lactoglobulin in the first month of life. Specific IgG levels to low response antigens may also increase in normal infants receiving dietary nucleotide containing formulas.

Mechanistically, in vitro and in vivo observations are thought to involve nucleotide effects on T-helper-cells at antigen presentation, modulations via interactions with cell surface molecules of T-cells, suppressed nonspecific activation of T-cells in response to antigen stimulus, and increased specific antibody response mediated through resting T-cells. Therefore, dietary nucleotides may favor the balance of T-cell differentiation to T-helper-2 cells which are primarily involved in B cell response. Thus, it is clear that nucleotides, as well as phytochemicals, can present several physiological benefits to patients having any of the above-mentioned conditions.

The skilled artisan will appreciate that any known fruits and vegetables may be used in the present nutritional compositions. Further, the skilled artisan will also appreciate that the fruits and/or vegetables may be provided in any amounts effective to provide nutrients to achieve the advantages described above. The skilled artisan will also appreciate that the major sources of nucleotides include red meats, organ meats, poultry, fish, shellfish, lentils, beans, asparagus, etc. In an embodiment, the nutritional compositions of the present disclosure may provide nucleotides in an amount of at least about 10 mg/100 kcal. In an embodiment, the nutritional compositions include from about 13 mg/100 kcal to about 19 mg/100 kcal nucleotides. In an embodiment, the nutritional compositions provide about 16 mg/100 kcal nucleotides.

In another embodiment, the nutritional compositions may include polymeric forms of nucleotides. The nucleotides may be present in amounts from about 0.9 to about 1.5 g/1000 kcal. In an embodiment, the nucleotides may be present in amounts up to about 1.2 g/1000 kcal. As discussed above, the skilled artisan will appreciate that although fruits and vegetables may provide an amount of nucleotides, exogenous synthesis may also constitute a major source of nucleotides.

In an embodiment, the nutritional compositions of the present disclosure may be hypocaloric (e.g., characterized by a low number of dietary calories) in order to provide a patient with proper nutrients but to manage weight gain without compromising musculoskeletal health. Typically, hypocaloric diets usually provide between 1,000 and 1,200 kcal/day. The present nutritional compositions may have caloric densities that range from about 0.3 to about 1.0 kcal/ml. In an embodiment, the nutritional compositions have a caloric density from about 0.5 to about 0.8 kcal/ml. The tube feed formula may also be of average to high energy density, from about 1.0 kcal/mL to 2.0 kcal/mL.

Osmolality is a measure of the osmoles of solute per kilogram of solvent (osmol/kg tube feeding or Osm/kg tube feeding). In an embodiment, the present nutritional compositions may have an osmolality that is less than or equal to 800 mOsm/kg water. In another embodiment, the present nutritional compositions have an osmolality that is less than or equal to 400 mOsm/kg water. In another embodiment, the present nutritional compositions have an osmolality that is less than or equal to 380 mOsm/kg water.

In an embodiment, the nutritional compositions further include one or more prebiotics. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, or combinations thereof.

The nutritional compositions may further include one or more probiotics. Non-limiting examples of probiotics include *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

One or more amino acids may also be present in the nutritional compositions. Non-limiting examples of amino acids include alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

The nutritional compositions may further include one or more synbiotics. Examples may include, for example, bifidobacteria and fructo-oligosaccharides ("FOS"); *Lactobacillus rhamnosus* GG and inulins; bifidobacteria or lactobacilli with FOS; or inulins or galactooligosaccharides ("GOS").

One or more antioxidants may also be present in the nutritional compositions. Non-limiting examples of ingredients with antioxidant activities selected from the group consisting of herbs, spices, and flavorings, carotenoids, flavonoids, polyphenols, lignan, lutein, lycopene, quercetin, limonin, coenzyme Q10 ("CoQ10"), glutathione, Goji (wolfberry), lactowolfberry, hesperidine, selenium, vitamin A, vitamin C, vitamin E, or combinations thereof. In an embodiment, the herbs, spices, and flavorings may be selected from the group consisting of garlic, cinnamon, ginseng, turmeric, curcumin, rosemary, mint, lemongrass, ginkgo, ginger, or combinations thereof.

The nutritional compositions also include fiber or a blend of different types of fiber. The fiber blend may contain a mixture of soluble and insoluble fibers. Soluble fibers may include, for example, fructooligosaccharides, acacia gum, inulin, etc. Insoluble fibers may include, for example, pea outer fiber.

As discussed above, the present compositions may also include a variety of herbs, spices and/or flavorings. Herbs that are included may be selected from angelica, bay laurel, chives, dill, catnip, fennel, lavender, lemon balm, majoram, mint, oregano, parsley, rosemary, rue, sage, tarragon, thyme, verbena, or combinations thereof. Spices may be selected from the group consisting of black pepper, cumin, cardamom, cayenne, celery seeds, chili pepper, cinnamon, clove, cumin, garlic, ginger, mustard, nutmeg, onion, paprika, peppercorns, tabasco, tumeric or combinations thereof. Flavorings may be any natural or artificial flavors or flavor enhancers such as, for example, MSG, vanilla extract, etc. The skilled artisan will appreciate that many herbs, spices and flavorings may overlap in uses such that, for example, a typical herb may be used as a spice.

The present compositions may further include a source of ω-3 polyunsaturated fatty acids including, but not limited to, α-linolenic acid ("ALA"), eicosatetraenoic acid ("ETA"), eicosapentaenoic acid ("EPA"), docosapentaenoic acid ("DPA"), docosahexaenoic acid ("DHA"), tetracosapentaenoic acid, tetracosahexaenoic acid (nisinic acid), or combinations thereof. Sources of ω-3 fatty acids include fish oil, poultry, eggs, or other plant or nut sources such as flax seed, walnuts, almonds, algae, krill, modified plants, or combinations thereof. The present compositions may also include conjugated linoleic acid ("CLA"). CLA is a naturally occurring lipid that supports lean body mass and immune function. Grass-fed beef is a good source of CLA.

The present compositions may also include monounsaturated fatty acids including, for example, palmitoleic acid, cis-vaccenic acid, and oleic acid. Common sources of monounsaturated fatty acids include, but are not limited to, natural foods such as nuts and avocados, and monounsaturated fatty acids are the main component of tea seed oil and olive oil (oleic acid). Canola oil is 57%-60% monounsaturated fat, olive oil is about 75% monounsaturated fat while tea seed oil is commonly over 80% monounsaturated fat. Other sources of monounsaturated fatty acids include macadamia nut oil, grapeseed oil, groundnut oil (peanut oil), sesame oil, corn oil, whole grain wheat, oatmeal, safflower oil, sunflower oil, tea-oil, and avocado oil.

As discussed above, the present disclosure also provides compositions and method that provide an emotional appeal for tube fed patients and/or their caretakers, as well as possible physiological benefits to the patient. In order to provide such an emotional appeal, the formulas of the present disclosure may, for example, 1) incorporate organic, natural and sustainable ingredients, 2) provide formulations that are specific to a certain ethnicity, use natural ingredients to provide coloring, 3) provide pediatric-friendly food blends and/or packaging that a parent would consider "normal" for children consuming an oral diet, 4) provide a component that allows for oral stimulation and a natural response to eating, and/or 5) provide methods of tube feeding that mimic typical meal times or a cycling menu.

One manner in which a nutritional composition (e.g., a tube feed formulation) may evoke an emotional appeal (and/or potential physiological benefit) is to provide organic, natural and sustainable ingredients. For example, compositions of the present disclosure may include 100% organic fruits and/or vegetables and organic meat products such as chicken or beef. To be certified organic, ingredients must be grown and manufactured according to country-specific standards. The United States Department of Agriculture ("USDA") Organic Certified Fruits and vegetables or Meat provides that fruits and vegetables must be grown without synthetic or non-organic pesticides, insecticides or herbicides.

For organic meat, the USDA provides that meat must be grown without the use of antibiotics and growth hormones. Organic products are typically free of artificial food additives, and are processed with fewer artificial methods such as chemical ripening, food irradiation, genetically modified organisms, etc. In an embodiment, the compositions of the present disclosure may include meat that is obtained from free range chicken and/or grass-fed beef and milk. Standards such as these, although not necessary, are more aligned with the current marketing message of "the way nature intended." Indeed, it is known that a cow's rumen is not intended to process grains, and these standards assure that the meat is raised without the use of antibiotics and growth hormones. See, Steve Windley, *Grass-fed Beef*, purehealthMD.com (2008).

Similarly, all natural ingredients may be used in the coloring of present compositions to avoid the chemicals in artificial coloring. For example, to achieve a composition with red color, amaranth, beets, or hibiscus may be added to the compositions. Alternatively, to achieve a composition with yellow/orange color, tumeric may be added to the compositions. The skilled artisan will appreciate that these are merely examples of color-providing fruits/vegetables and that any known fruits or vegetables capable of providing color to the compositions may be used.

Another manner in which a nutritional composition may evoke an emotional appeal (and/or potential physiological benefit) is to create ethnicity specific tube feed formulas. In an embodiment, the present compositions are formulated with fruits, vegetables, macronutrient sources and spices typically consumed in specific regions of the world. For example, a tube feed formulation may include curcumin or tumeric and be marketed as an Indian cuisine formulation. Curcumin is a component of the spice tumeric (*curcuma longa*) and is responsible for the yellow color of curry. Curcumin has specifically been shown to possess anti-inflammatory, antioxidant and anti-proteolytic properties. With regards to long-term, tube fed pediatric patients who experience profound decrements in lean body mass, for example, curcumin may provide some attenuation of skeletal muscle proteolysis. Importantly, curcumin has been shown to antagonize the upregulation of nuclear factor-κβ (NF-κβ) and this gene is inextricably tied to initiating an intracellular signaling cascade responsible for inducing skeletal muscle atrophy during unloading conditions. See, Farid, et al., *Effects of dietary curcumin or N-acetylcysteine on NF-κB activity and contractile performance in ambulatory and unloaded murine soleus*, J. Clin. Invest., 114(10):1504-11 (2005).

Similarly, cumin, oregano and chili powder may be included in compositions that are marketed as a Mexican cuisine formulation. Other cuisine options include, but are not limited to, Thai, Italian, Mediterranean, or American.

Another manner in which a nutritional composition may evoke an emotional appeal is to include pediatric-friendly food blends, or foods that parents would consider "normal" for kids consuming an oral diet. Popular branded foods include, for example, Cheerios®, Juicy Juice®, Campbell's Alphabet Soup™, chicken nuggets, strawberry shortcake, bananas, apple sauce, etc.

Yet another manner in which a nutritional composition may evoke an emotional appeal (and/or potential physiological benefit) is to provide an extra, add-on component that has at least one characteristic selected from the group consisting of visually appealing/appetizing, an appealing aroma, an appealing flavor or smell to stimulate the natural response to eating, or combinations thereof. These components (smell, taste, thought, etc.) may also have physiological benefits such that they elicit the cephalic phase or the first part of digestion, which would allow the patient begin the digestive processes in a more similar way to an oral diet. Therefore, digestive processes begin with the sight, smell or thought of food and physiological processes occur to prime the body for digestion (e.g., salivation, gastric acid secretion, pancreatic endocrine and exocrine).

The add-on component may be a tablet, lozenge, dissolvable strip, or chewing gum. It may or may not be nutritive or contain calories. If intended for a strictly Nothing Per Orem ("NPO") patient, the add-on component could be tailored to ensure compliance (e.g., provide dissolvable strip form).

The aroma may be any aroma known in the art. For example, the aroma may be a dessert aroma such as, but not limited to vanilla, chocolate, strawberry, lemon, custard, etc. The aroma may also be related to an ethnic food such as, for example, curry, chili powder, roasted red pepper, basil, etc. In another embodiment, the aroma may be an aroma that is associated with common American foods such as, but not limited to, meatloaf, chicken, roast, mashed potatoes, etc. By providing a wide range of aromas, the patients may be able to select an aroma that sounds satisfying to the patient at the time of tube feeding. The aroma may be released upon opening the packaging, or the smell may be enhanced by a "scratch-and-sniff" device.

The packaging of the tube feeding formula, for example, and add-on device can be designed to mimic a meal. For example, the tube feed formula could simulate the appearance of a plate in that it may be a circular, flat package with pictures of meal contents. The patient could sit down for dinner with a "plate of food." The add-on package may be any shape or size known in the art and may be sized and shaped to simulate the appearance of a food item or an eating utensil. In this way, the tube feeding package would mimic a meal and include an extra, add-on component (e.g., lozenge, dissolvable strip, chewing gum) that, upon opening/consuming, would release a food scent. The patient would put the lozenge, dissolvable strip, chewing gum in his/her mouth for flavor. This would allow for a more "natural" eating routine and stimulate the natural response to eating (e.g., the cephalic phase, smell, taste, thought, etc.). The skilled artisan will appreciate that the add-on package need not have a particular shape, may have any size and shape known in the art, or may be sold separately from the tube feeding formula.

Benefits of the add-on component relate to simulation of the cephalic phase, and promotion of oral health. Methods of current formula delivery include delivery directly into the GI tract which bypasses this first phase of digestion, the cephalic phase. The cephalic phase of digestion results in gastric acid secretion, release of pancreatic enzymes including insulin and therefore, may improve digestion and tolerance to the formula. With bypassing of this first phase of digestion, it could be theorized that there are several physiological consequences. First, with bypassing of peristalsis in the esophagus, it could be theorized that "pacing" is affected throughout the GI tract. Second, without use, there could be atrophy of the oral/GI muscles which would result in delayed recovery or may be problematic upon resumption of an oral diet. Third, with the discovery of taste receptors in the gut, there may be missing communication between the mouth and gut taste receptors. Lastly, particularly in diabetic patients and related to early release of insulin during the cephalic phase, there may dysregulation in glycemic control.

Moreover, the use of the add-on component may also enhance oral health (components including saliva production and oral microbiota) which is important for several areas of health, and has been found to be a predictor of mortality. See, Awano S, et al., *Oral health and mortality risk from pneumonia in the elderly*, J. Dent. Res., 87(4): 334-339 (2008); Ide R, et al., *Oral symptoms predict mortally: a prospective study in Japan*, J. Dent. Res. 87(5):485-489 (2008). Patients on tube feedings, for example, are at higher risk for poor oral health and have a higher prevalence reported of gram negative bacteria. See, Leibovitz A, et al., *Saliva secretion and oral flora in prolonged nasogastric tube-fed elderly patients*, IMAJ, 5:329-332 (2003). Reduced salivary flow or poor oral health are associated with several conditions, which may be common to individuals on long term tube feedings, including history of radiation to head and neck, diseases of salivary gland, cystic fibrosis, alcoholic cirrhosis, as well as medication usage including anticholinergics, antidepressants, antipsychotics, diuretics, antihypertensives, antihistamines, and nonsteroidal anti-inflammatory medications.

The flavor and scent of the add-on component may or may not be similar to the foods present in the tube feeding. In this manner, the add-on component comes with a variety of flavors for emotional appeal, which allows the patient to choose what they are hungry for. For example, if the tube feed formulation contains chicken, the add-on component may smell like chicken. The add-on component may have a strong flavor to stimulate saliva production. The strong flavor may be, for example, tart, ginger, etc.

Since the add-on component may be placed directly into the mouth of the patient, the add-on component may include functional ingredients as well. For example, the functional ingredients may include probiotics to maintain healthy oral microflora, or capsaisin to trigger the swallow reflex.

In an embodiment, the dissolvable strip would be used when oral intake is contraindicated (e.g., dysphagia, neurological impairment).

These types of extra, add-on components may be used when oral intake is contraindicated and may allow for tube feed formulations that are specifically designed to mimic the eating process, which primes the body to absorb and use nutrients. In an embodiment, the add-on component may be a flavor tab that is packaged in a wrapper and releases a scent when opened. The flavor tab may also create a range of flavors for the patient including, for example, chicken seasoned with parsley, mashed potatoes, etc. Based on the perceived scents and flavors, the patient can select what types of flavors they are "hungry" for. In an embodiment, the add-on component (e.g., flavor tab) is used just prior to and during tube feeding administration. The flavor tab can be calorie free and may only contain ingredients allowed on a Nothing Per Orem ("NPO") diet.

Physiological feeding includes introduction of routine and variety into the diet. The idea includes bolus feeding which resembles the breakfast, lunch, dinner, snack pattern in which an enteral formulation is designed to include a variety of food components representative of a varied, mixed, cycle menu diet. A variety of bolus feeding may change depending on meal or week. The variety of food in the menu cycle may be further specialized and diversified by including ethnic food and various spices. This regimen incorporates benefits of whole food beyond basic nutrients and provides a source of phyto- and zoo-chemicals with health benefits. The benefits include, but are not limited to oxidative stress modulation with benefits related to musculoskeletal health, blood pressure, cholesterol levels, glycemic control, cancer, cognitive function, inflammation.

Along these lines, another manner in which to evoke an emotional appeal is to provide methods of administering nutritional compositions (e.g., tube feedings) that mimic regular meal times, or create a cycling menu with unique foods, as mentioned above. For example, in an embodiment, the tube feed formulations may be administered three times daily at normal meal times of breakfast, lunch and dinner, and/or with several snacks. Similarly, the present compositions may be packaged with an appealing or appetizing label or product name.

In another embodiment, the tube feedings may be administered such that the administration creates a cycling menu with unique foods having, for example, different protein sources, and different fruits and vegetables. The skilled artisan will appreciate that many different combinations of whole foods may be used in the present compositions. Different examples of such combinations include, as with Clinutren Mix products, but are not limited to, turkey with mixed vegetables, veal with broccoli, spring vegetables stew, cod with leek, Hungarian beef, salmon and spinach, chicken and vegetables, and beef and carrots.

In another example, the tube feedings may be administered at normal meal times. For example, a first feeding may be administered at a typical breakfast time in the morning. A second feeding may be administered at a typical lunch time around noon, and a third feeding may be administered at a typical dinner time in the evening. The tube feeding formula may also be administered at several additional times, mimicking snack times.

The formulation of nutritional compositions of the present disclosure may be varied from feeding to feeding, day to day, week to week, or month to month to provide a patient with a variety of food, which provide a variety of different nutrients. For example, daily feedings may be varied as follows: a first daily feeding (e.g., at breakfast time) may be the same as or different from a second daily feeding (e.g., at lunch time), which may be the same as or different from a third daily feeding (e.g., at dinner time). Daily feedings may also vary by providing a first feeding (e.g., at breakfast time) on day one that is the same as or different from a first feeding (e.g., at breakfast time) on day two. The same goes for second and third daily feedings.

In another embodiment, feedings may vary from week to week or month to month. In this regard, a patient may be administered a specific tube feed formulation for a week or a month before the formulation changes to a second formulation. Similarly, the patient may be administered a daily feeding menu of first, second and third feedings, wherein each first feeding is the same for a week or a month, each second feeding is the same for a week or a month, and each third feeding is the same for a week or a month before the feedings are changed to a second formulation.

The changing of a first formulation to a second formulation, regardless of how frequently the formulations are changed, may include changing of a specific component of the formulation. For example, a tube feed formulation may be administered to a patient on day one that has a certain amounts of protein, carbohydrates and fats. On day two, a similar tube feed formulation may be administered to the patient that has the same amount of protein and carbohydrates, but an increased or decreased amount of fats. In this manner, the amounts of macro and micronutrients in the nutritional compositions of the present claims may vary from formula to formula. In an embodiment, at least one source of protein of a nutritional composition is different than a new, or second, nutritional composition. In an embodiment, at least one source of carbohydrates of a nutritional composition is different than a new, or second, nutritional composition. In an embodiment, at least one source of fats of a nutritional composition is different than a new, or second, nutritional composition.

The nutritional compositions can be administered to an individual having a preexisting medical condition, or at risk of developing a medical condition, or having characteristics common to patients on long term tube feeding formulas. The underlying medical condition may be, for example, cerebral palsy, failure-to-thrive, neuromuscular disorders, brain injury, developmental delay, immune deficiency or dysregulation, compromised musculoskeletal and gut health, low bone density, pressure ulcers, chronic wounds, insulin resistance, or combinations thereof. The nutritional composition can be a formulation designed for any mammal such as a human or an animal. In an embodiment, the nutritional composition is a tube-feed formulation.

Methods of improving the overall health of a patient having an underlying medical condition are also provided. The methods include administering to a patient having an underlying medical condition a tube feed formulation having at least five different whole food components, a source of protein, a source of fat, a source of carbohydrate, a source of fiber and a source of vitamins or minerals. The formulation includes at least five, six, seven, or eight different whole food components and the whole food components may be selected from the group consisting of a processed fruit, a processed vegetable, a processed meat, a processed grain, or combinations thereof.

Methods of improving the overall health of a patient having an underlying medical condition are also provided. The methods include administering to a patient having an underlying medical condition a tube feed formulation having a processed whole food, at least seven different sources of macronutrients selected from the group consisting of protein, carbohydrates, fats, fibers, or combinations thereof, and a source of vitamins or minerals. The at least seven different sources of macronutrients includes at least one protein, at least one carbohydrate and at least one fat. The at least seven different sources of macronutrients may also include at least three different proteins and/or at least three different carbohydrates and/or at least three different fats.

Methods of administering tube feeding formulations are also provided. The methods include administering a first tube feed formulation having a whole food to a patient at a first time of a day corresponding to a typical breakfast time, administering a second tube feed formulation having a whole food to the patient at a second time of the day corresponding to a typical lunch time, and administering a third tube feed formulation having a whole food to the patient at a third time of the day corresponding to a typical dinner time. The first, second and third tube feed formulations include at least one protein, and at least one of a fruit and a vegetable. The protein of each of the first, second and third tube feed formulations may be different. The at least one of a fruit and a vegetable of each of the first, second and third tube feed formulations may also be different. The tube feeding formula may also be administered at several additional times with different fruits and vegetables and macronutrient sources, mimicking snack times. In this manner, the methods may include administering fourth, fifth, sixth, etc. formulations correlating with typical daily snack times.

The nutritional compositions of the present claims may be administered at a temperature that is either warm or cold. It can be theorized that differences in food temperature of a meal containing protein, fat, carbohydrate and whole food components may impact digestion and physiological response. Indeed, prior research has shown that temperature (hot, warm, cold) of a simple food beverage, sweetened instant coffee, administered via nasogastric tube did not impact gastric acid secretion, serum gastrin concentrations, or gastric emptying. See, K. McArthur, et al., *Gastric acid secretion, gastrin release, and gastric emptying in humans as affected by liquid meal temperature*, Am. J. Clin. Nutr., 49:51-54 (1989).

The present disclosure also provides tube feed packages. The packages include a first component contained in the package that is a tube feed formulation. The package may resemble the shape of a plate or food item or combinations thereof. The package further includes a second component contained with or attached to the first component, or purchased separately. The second component is comprised of a substance that is consumed by mouth and has a flavor/taste and an aroma and being packaged separately from the first component. The second component may be a tablet or lozenge, dissolvable strip or chewing gum and would be tailored to be NPO-compliant when necessary and may be contained in a package of a particular size or shape.

By using the improved compositions and methods of administering same, Applicant is able to provide improved nutritional compositions to adult and pediatric patients that have an increased number and variety of fruits and vegetables, an increased variety of macronutrient sources, and the addition of other components found in whole foods. The improved formulations help to mimic a "whole food" tube feeding that best meets the nutritional needs of the target population and also provides physiological benefits and emotional appeal.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A tube feed package comprising:
a first component contained in a first package and comprising a tube feed formulation having a processed whole food, the first component having an osmolality up to 400 mOsm/kg water; and
a second component contained in a second package that is separate from the first package of the first component, the second component being an orally dissolvable strip.

2. The tube feed package according to claim 1, wherein the flavor of the second component corresponds to the processed whole food of the tube feed formulation.

3. The tube feed package according to claim 1, wherein the flavor and/or scent of the second component corresponds to a nutrient source that is typically consumed by individuals in a specific region of the world.

4. The tube feed package according to claim 1, wherein the second component is compliant with a nothing per orem ("NPO") diet.

5. The tube feed package according to claim 1, wherein the second component includes a functional ingredient selected from the group consisting of probiotics, capsaisin, a source of strong flavor, and combinations thereof.

6. The tube feed package according to claim 5, wherein the strong flavor is one of tart and ginger.

7. The tube feed package according to claim 1, wherein the second component is contained in a package having a shape of an eating utensil selected from the group consisting of a plate, a spoon, a fork, a knife, and combinations thereof.

8. The tube feed package according to claim 1, wherein the second component is calorie free.

9. A tube feed package comprising:
a first component contained in a first package and comprising a tube feed formulation having a processed whole food, the first component having an osmolality up to 400 mOsm/kg water; and
a second component packaged in a second package that is separate from the first package of the first component for placing into a mouth of a patient, the second component being an orally dissolvable strip and comprising a substance having an aroma.

10. The tube feed package according to claim 9, wherein the second component is not edible.

11. The tube feed package according to claim 9, wherein the aroma of the second component corresponds to a typical aroma of the processed whole food of the tube feed formulation.

12. The tube feed package according to claim 9, wherein the aroma of the second component corresponds to a nutrient source that is typically consumed by individuals in a specific region of the world.

* * * * *